US008845672B2

(12) United States Patent
Alverdy

(10) Patent No.: US 8,845,672 B2
(45) Date of Patent: Sep. 30, 2014

(54) BALLOON SYSTEM AND METHODS FOR TREATING OBESITY

(75) Inventor: John C. Alverdy, Glenview, IL (US)

(73) Assignee: ReShape Medical, Inc., San Clemente, CA (US)

(*) Notice: Subject to any disclaimer, the term of this patent is extended or adjusted under 35 U.S.C. 154(b) by 416 days.

(21) Appl. No.: 12/625,473

(22) Filed: Nov. 24, 2009

(65) Prior Publication Data
US 2010/0130998 A1 May 27, 2010

Related U.S. Application Data

(63) Continuation-in-part of application No. 12/257,724, filed on Oct. 24, 2008, now abandoned, which is a continuation-in-part of application No. 10/513,583, filed as application No. PCT/US03/12782 on Apr. 25, 2003, now abandoned.

(60) Provisional application No. 60/379,540, filed on May 9, 2002.

(51) Int. Cl.
A61M 29/00 (2006.01)
A61F 5/00 (2006.01)

(52) U.S. Cl.
CPC .................. *A61F 5/003* (2013.01); *A61F 5/004* (2013.01)
USPC ........................................ 606/192; 604/96.01

(58) Field of Classification Search
USPC ......... 606/159, 192; 604/96.01, 909; 128/897
See application file for complete search history.

(56) References Cited

U.S. PATENT DOCUMENTS

| 2,493,326 A | 1/1950 | Trinder |
| 4,133,315 A | 1/1979 | Berman et al. |
| 4,246,893 A | 1/1981 | Berson |
| 4,356,824 A | 11/1982 | Vazquez |
| 4,416,267 A | 11/1983 | Garren et al. |
| 4,485,805 A | 12/1984 | Foster, Jr. |
| 4,598,699 A | 7/1986 | Garren et al. |
| 4,694,827 A * | 9/1987 | Weiner et al. ............. 606/192 |
| 4,723,547 A | 2/1988 | Kullas et al. |
| 4,899,747 A | 2/1990 | Garren et al. |

(Continued)

FOREIGN PATENT DOCUMENTS

| DE | 8708978 U1 | 11/1987 |
| EP | 0 457 456 | 5/1990 |

(Continued)

OTHER PUBLICATIONS

Wahlen Ch et al. "The BioEnterics Intragastric Balloon: How to use it" Obesity Surgery 2001;11:524-527.

(Continued)

*Primary Examiner* — Thomas McEvoy
*Assistant Examiner* — Julie A Szpira
(74) *Attorney, Agent, or Firm* — Perkins Coie LLP

(57) ABSTRACT

A medical system for the treatment of morbid obesity comprising an inflatable balloon implanted in a gastric cavity, a percutaneous fillant delivery tube and a control module connected to the tube for regulating the inflation and deflation of the balloon. The balloon may be individually contoured and inflated to occupy a large volume of the gastric cavity to provide a feeling of satiety. The balloon may also be deflated to give the gastric cavity lining a rest during less critical time.

6 Claims, 2 Drawing Sheets

(56) References Cited

U.S. PATENT DOCUMENTS

Figure 1:
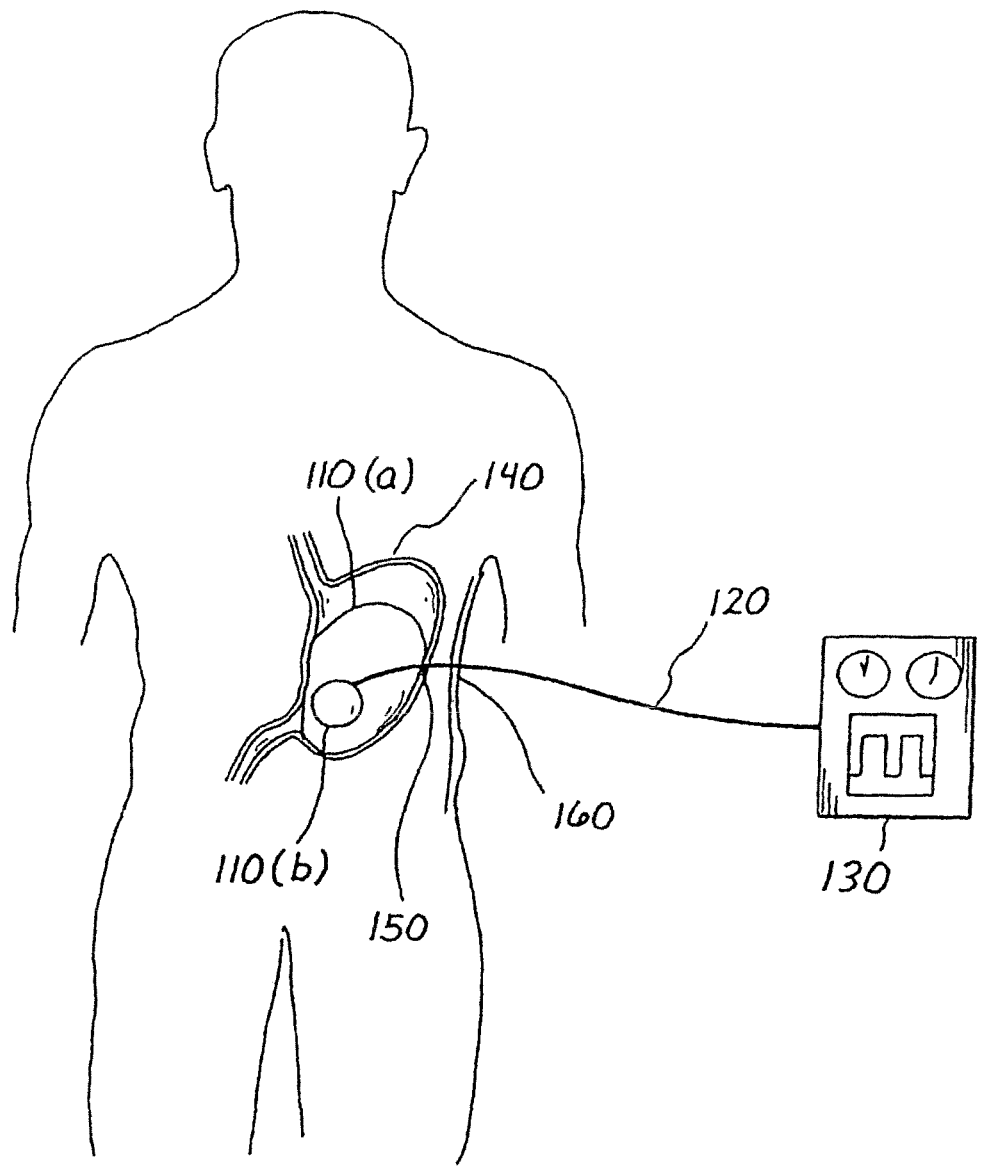

| | | | |
|---|---|---|---|
| 4,940,458 A | 7/1990 | Cohn | |
| 5,084,061 A | 1/1992 | Gau et al. | |
| 5,123,840 A | 6/1992 | Nates | |
| 5,259,399 A * | 11/1993 | Brown | 128/897 |
| 5,263,934 A | 11/1993 | Haak | |
| 5,273,536 A | 12/1993 | Savas | |
| 5,318,530 A | 6/1994 | Nelson, Jr. | |
| 5,334,187 A | 8/1994 | Fischell et al. | |
| 5,431,173 A | 7/1995 | Chin et al. | |
| 5,496,271 A | 3/1996 | Burton et al. | |
| 5,575,772 A | 11/1996 | Lennox | |
| 5,643,209 A | 7/1997 | Fugoso et al. | |
| 5,730,722 A | 3/1998 | Wilk | |
| 5,779,728 A | 7/1998 | Lunsford et al. | |
| 5,857,991 A | 1/1999 | Grothoff et al. | |
| 5,876,376 A | 3/1999 | Schwab et al. | |
| 5,938,669 A | 8/1999 | Klaiber et al. | |
| 5,993,473 A * | 11/1999 | Chan et al. | 606/192 |
| 6,149,621 A | 11/2000 | Makihara | |
| 6,254,355 B1 | 7/2001 | Gharib | |
| 6,276,567 B1 | 8/2001 | Diaz et al. | |
| 6,280,411 B1 | 8/2001 | Lennox | |
| 6,423,058 B1 | 7/2002 | Edwards et al. | |
| 6,454,785 B2 | 9/2002 | De Hoyos Garza | |
| 6,524,234 B2 | 2/2003 | Ouchi | |
| 6,535,764 B2 | 3/2003 | Imran et al. | |
| 6,547,788 B1 | 4/2003 | Maguire et al. | |
| 6,579,301 B1 | 6/2003 | Bales et al. | |
| 6,613,018 B2 | 9/2003 | Bagga et al. | |
| 6,613,037 B2 | 9/2003 | Khosravi et al. | |
| 6,706,010 B1 | 3/2004 | Miki et al. | |
| 6,746,460 B2 * | 6/2004 | Gannoe et al. | 606/153 |
| 6,826,428 B1 | 11/2004 | Chen et al. | |
| 6,850,128 B2 | 2/2005 | Park | |
| 6,866,657 B2 | 3/2005 | Shchervinsky | |
| 6,869,431 B2 | 3/2005 | Maguire et al. | |
| 6,890,300 B2 | 5/2005 | Lloyd et al. | |
| 6,890,346 B2 | 5/2005 | Ganz et al. | |
| 6,923,754 B2 | 8/2005 | Lubock | |
| 6,939,299 B1 | 9/2005 | Petersen et al. | |
| 6,958,052 B1 | 10/2005 | Charlton | |
| 7,001,419 B2 | 2/2006 | DiCaprio et al. | |
| 7,016,735 B2 | 3/2006 | Imran et al. | |
| 7,020,531 B1 | 3/2006 | Colliou et al. | |
| 7,033,373 B2 | 4/2006 | de la Torre et al. | |
| 7,056,305 B2 * | 6/2006 | Garza Alvarez | 604/191 |
| 7,076,305 B2 | 7/2006 | Imran et al. | |
| 7,131,945 B2 | 11/2006 | Fink et al. | |
| 7,483,746 B2 | 1/2009 | Lee et al. | |
| 7,828,749 B2 | 11/2010 | Douglas et al. | |
| 2001/0022988 A1 | 9/2001 | Schwarz et al. | |
| 2001/0037127 A1 * | 11/2001 | De Hoyos Garza | 606/192 |
| 2002/0055757 A1 * | 5/2002 | Torre et al. | 606/192 |
| 2002/0107515 A1 | 8/2002 | Edwards et al. | |
| 2002/0161388 A1 | 10/2002 | Samuels et al. | |
| 2002/0173804 A1 | 11/2002 | Rousseau | |
| 2003/0114878 A1 | 6/2003 | Diederich et al. | |
| 2003/0171768 A1 | 9/2003 | McGhan | |
| 2003/0187390 A1 | 10/2003 | Bates et al. | |
| 2004/0044354 A1 | 3/2004 | Gannoe et al. | |
| 2004/0059289 A1 | 3/2004 | Garza Alvarez | |
| 2004/0059290 A1 | 3/2004 | Palasis | |
| 2004/0073162 A1 | 4/2004 | Bleam et al. | |
| 2004/0087902 A1 | 5/2004 | Richter | |
| 2004/0106899 A1 | 6/2004 | McMichael et al. | |
| 2004/0116897 A1 | 6/2004 | Aboul-Hosn | |
| 2004/0127915 A1 | 7/2004 | Fleenor et al. | |
| 2004/0186502 A1 | 9/2004 | Sampson et al. | |
| 2004/0220665 A1 | 11/2004 | Hossainy | |
| 2004/0236280 A1 | 11/2004 | Rice et al. | |
| 2004/0236361 A1 | 11/2004 | Sakurai | |
| 2004/0254600 A1 | 12/2004 | Zarbatany et al. | |
| 2005/0027283 A1 | 2/2005 | Richard et al. | |
| 2005/0027313 A1 | 2/2005 | Shaker | |
| 2005/0038415 A1 | 2/2005 | Rohr et al. | |
| 2005/0055039 A1 | 3/2005 | Burnett et al. | |
| 2005/0059990 A1 | 3/2005 | Ayala et al. | |
| 2005/0075624 A1 | 4/2005 | Miesel | |
| 2005/0085792 A1 | 4/2005 | Gershowitz | |
| 2005/0119674 A1 | 6/2005 | Gingras | |
| 2005/0131442 A1 | 6/2005 | Yachia et al. | |
| 2005/0143784 A1 | 6/2005 | Imran | |
| 2005/0159769 A1 | 7/2005 | Alverdy | |
| 2005/0177103 A1 | 8/2005 | Hunter et al. | |
| 2005/0192615 A1 | 9/2005 | Torre et al. | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2006/0058829 A1 | 3/2006 | Sampson et al. | |
| 2006/0184112 A1 | 8/2006 | Horn et al. | |
| 2006/0259020 A1 | 11/2006 | Sharratt | |
| 2007/0016262 A1 | 1/2007 | Gross et al. | |
| 2007/0093728 A1 | 4/2007 | Douglas et al. | |
| 2007/0100367 A1 | 5/2007 | Quijano | |
| 2007/0100368 A1 | 5/2007 | Quijano | |
| 2007/0100369 A1 | 5/2007 | Cragg | |
| 2007/0142770 A1 | 6/2007 | Rioux et al. | |
| 2007/0149994 A1 | 6/2007 | Sosnowski | |
| 2007/0173881 A1 | 7/2007 | Birk et al. | |
| 2007/0233161 A1 | 10/2007 | Weller et al. | |
| 2007/0250020 A1 | 10/2007 | Kim et al. | |
| 2007/0265369 A1 | 11/2007 | Muratoglu et al. | |
| 2007/0265598 A1 | 11/2007 | Karasik | |
| 2007/0288033 A1 | 12/2007 | Murature et al. | |
| 2008/0058887 A1 | 3/2008 | Griffin et al. | |
| 2008/0082056 A1 | 4/2008 | Mauch et al. | |
| 2008/0097513 A1 | 4/2008 | Kaji et al. | |
| 2008/0119729 A1 | 5/2008 | Copa et al. | |
| 2008/0172079 A1 | 7/2008 | Birk | |
| 2008/0190363 A1 | 8/2008 | Chen et al. | |
| 2008/0208241 A1 | 8/2008 | Weiner et al. | |
| 2008/0233167 A1 | 9/2008 | Li et al. | |
| 2008/0243071 A1 | 10/2008 | Quijano | |
| 2008/0243166 A1 | 10/2008 | Paganon et al. | |
| 2008/0255601 A1 | 10/2008 | Birk | |
| 2008/0319471 A1 | 12/2008 | Sosnowski | |
| 2009/0048624 A1 | 2/2009 | Alverdy | |
| 2009/0275973 A1 | 11/2009 | Chen et al. | |
| 2010/0023047 A1 | 1/2010 | Simpson | |
| 2010/0130998 A1 | 5/2010 | Alverdy | |
| 2010/0243135 A1 | 9/2010 | Pepper et al. | |
| 2010/0251837 A1 | 10/2010 | Bouasaysy et al. | |
| 2011/0178544 A1 | 7/2011 | Sosnowski et al. | |
| 2012/0271336 A1 | 10/2012 | Hamman et al. | |
| 2012/0289992 A1 | 11/2012 | Quijano et al. | |

FOREIGN PATENT DOCUMENTS

| | | |
|---|---|---|
| EP | 0 485 903 | 8/1991 |
| FR | 2862525 A1 | 5/2005 |
| GB | 2 139 902 A | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| WO | 0166166 A2 | 9/2001 |
| WO | WO 2006035446 | 4/2006 |
| WO | WO-2006056944 A1 | 6/2006 |
| WO | WO 2006/128978 | 12/2006 |
| WO | 2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | 2008042819 A2 | 4/2008 |
| WO | WO-2008121831 A1 | 10/2008 |
| WO | WO-2009112786 A2 | 9/2009 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011024077 A2 | 3/2011 |

(56) References Cited

FOREIGN PATENT DOCUMENTS

| WO | WO-2011038270 A2 | 3/2011 |
|---|---|---|
| WO | WO-2011097637 A1 | 8/2011 |
| WO | WO-2011127205 A1 | 10/2011 |
| WO | WO-2012048226 A1 | 4/2012 |

OTHER PUBLICATIONS

Patient information "Living with the BIB" by INAMED Health (2004).
International Search Report; International Application No. PCT/US2011/024082, Applicant: ReShape Medical, Inc., Mailing Date Apr. 6, 2011, 10 pages.
International Search Report; International Application No. PCT/US2011/024077; Applicant: ReShape Medical, Inc., Mailing Date Apr. 6, 2011, 12 pages.
International Search Report; International Application No. PCT/US2010/042948; Applicant: ReShape Medical, Inc., Mailing Date Apr. 1, 2011, 11 pages.
International Search Report; International Application No. PCT/US2010/043136; Applicant: ReShape Medical, Inc., Mailing Date Apr. 12, 2011, 9 pages.
International Search Report; International Application No. PCT/US20101043134; Applicant: ReShape Medical, Inc., Mailing Date Apr. 27, 2011, 12 pages.
International Search Report; International Application No. PCT/US2011/0426233; Applicant: ReShape Medical, Inc., Mailing Date Apr. 26, 2011, 9 pages.
"ReShape Inflatable Gastric Ballon Going on Trial as Weight Loss Option," MedGadget: Internet Journal of Emerging Medical Technologies. Feb. 4, 2010. (5 pages).
International Search Report; International Application No. PCT/US2008/058677, Applicant: ReShape Medical et al., Mailing Date Aug. 21, 2008, 12 pages.
International Search Report; International Application No. PCT/US2006/042710, Applicant: Abdominus, Inc. et al, Mailing Date Mar. 15, 2007, 9 pages.
International Search Report; International Application No. PCT/US2006/048647, Applicant: Abdominus, Inc. et al., Mailing Date May 22, 2007, 12 pages.
International Search Report; International Application No. PCT/US2008/068058, Applicant: ReShape Medical, Inc. et al, Mailing Date Nov. 19, 2008, 11 pages.
International Search Report; International Application No. PCT/US2006/042711, Applicant: Abdominus, Inc. et al, Mailing Date Mar. 16, 2007, 9 pages.
Supplementary European Search Report for EP 03726447.0, mailed Mar. 1, 2006.
International Search Report; International Application No. PCT/US2003/012782, Applicant: Applied Medical Resources Corporation, Mailing Date Oct. 28, 2003, 7 pages.
International Search Report; International Application No. PCT/US2006/042336, Applicant: Abdominus, Inc., Mailing Date Mar. 14, 2007, 9 pages.
International Search Report; International Application No. PCT/US2010/029865, Applicant: ReShape Medical, Inc., Mailing Date Jan. 5, 2011, 9 pages.
Final Office Action; U.S. Appl. No. 11/694,536, Mailing Date Mar. 11, 2011, 13 pages.
Final Office Action; U.S. Appl. No. 11/768,152, Mailing Date Jan. 19, 2011, 13 pages.
International Search Report; International Application No. PCT/US2010/050260; Applicant: ReShape Medical, Inc., Mailing Date: Jun. 17, 2011, 9 pages.
International Search Report; International Application No. PCT/US2011/031463; Applicant: ReShape Medical, Inc., Mailing Date: Jun. 27, 2011, 10 pages.
International Search Report; International Application No. PCT/US1155373, Applicant: Reshape Medical, Inc., dated: Jan. 20, 2012, 7 pages.
Non-Final Office Action; U.S. Appl. No. 11/694,536; dated: Oct. 26, 2011, 13 pages.
Non-Final Office Action; U.S. Appl. No. 11/263,302; dated: Oct. 9, 2012, 6 pages.
Non-Final Office Action; U.S. Appl. No. 12/723,545; dated Feb. 29, 2012, 10 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
Wahlen Ch et al. "The BioEnterics Intragastric Balloon: How to use it" Obesity Surgery 2001; 11:524-527.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
Extended European Search Report; Application No. EP11766679.2, Applicant: Reshape Medical, Inc., mailed Dec. 12, 2013, 6 pages.

\* cited by examiner

BALLOON SYSTEM AND METHODS FOR TREATING OBESITY

CROSS-REFERENCE TO RELATED APPLICATIONS

This application is a continuation-in-part application of U.S. patent application Ser. No. 12/257,724, filed Oct. 24, 2008, now abandoned, which is a continuation-in-part of U.S. patent application Ser. No. 10/513,583, filed Nov. 2, 2004, now abandoned, which is a U.S. National Phase Application under 35 U.S.C. §371 of International Application No. PCT/US2003/012782, filed Apr. 25, 2003, which claims the benefit of U.S. Provisional Application No. 60/379,540, filed May. 9, 2002. Each of the foregoing applications are incorporated herein by reference in their entireties.

BACKGROUND

1. Field

This invention generally relates to the treatment of morbid obesity and, more specifically, to a system and method for treating morbid obesity using a variably cycled percutaneous balloon implanted in the gastric cavity.

2. General Background

Morbid obesity is a major health problem confronting the general public and health care industry today. It is estimated that approximately 50% of the U.S. population is overweight and over ten million Americans are more than 100 pounds over their ideal weight. Generally, a person is considered morbidly (or seriously) obese if they are 100 pounds or more over their ideal weight. The morbidly obese group faces increased health risks including a higher likelihood of heart disease, hypertension, diabetes and certain cancers. Over 300,000 Americans die of obesity related illnesses each year. In addition, the morbidly obese generally have lower self-esteem and are more likely to suffer from depression than the general public.

Most obese individuals have struggled unsuccessfully with their weight for a lifetime. The numerous diets, behavioral therapy and treatments such as hypnosis, pituitary hormones and appetite suppressant drugs attest to the great difficulty many overweight people have in losing weight and keeping it off. Some of these weight loss strategies can be successful in the mildly obese people, but nearly all fail in individuals considered morbidly obese. These disappointing results have led many patients and their doctors to consider surgery as an option for weight loss.

Surgical techniques bring about weight loss primarily by limiting how much the stomach can hold. Today's most common surgical procedures to promote weight loss focus on decreasing food intake by restriction. Gastric banding, gastric bypass and vertical-banded gastroplasty are surgeries that limit the amount of food the stomach can hold by closing off or removing parts of the stomach. Other surgeries attempt to permanently fill the stomach with an inflated balloon. These treatments are invasive, require major surgery with hospitalization and are associated with complications.

The success rates of current treatments and procedures have been poor. With the restrictive procedure, the patient is usually limited to eating very small amounts of food at a time. For many people, this can create a "satisfied" feeling, but they often do not feel "full". The ability to eat a large amount of food at one time is lost; consequently, many patients return to eating excessive amounts of high calorie or high sugar liquid foods. Essentially, their diet includes milk shakes and ice cream.

As to the balloon procedure of the past, very limited positive results were achieved. The balloon was relatively small when compared to the overall volume of the morbidly obese stomach. This is due to physiological limitation on the balloon volume. That is, complications of the device precluded enlarging it to a volume that would occupy more of the stomach. Yet, in order for the balloon to achieve a patient's feeling of fullness and satiation, the balloon would need to occupy a large portion (volume) of the patient's stomach. A balloon occupying this much volume without fixation or an inflation/deflation cycling has the potential of blocking food flow and causing necrosis of the stomach wall, ulcers and/or bleeding.

Moreover, success depends on the ability of a treatment to "normalize" not only the mechanical and neurohormonal sensation of feeling full and satiated, but also involves psychological factors. Both the mechanical and neurohormonal factors relate to one's need to feel "full" and "satiated". Chemicals released by the stomach during the digestive process largely drive these factors. In other words, filling the stomach or limiting its pouch size controls these chemicals. Current surgical approaches, however, fail to achieve this global feeling of "satiety" response as they restrict food entry only into the small proximal stomach pouch and bypass the distal stomach where most of the neurohormonal chemical are normally released. Medical therapy is focused almost exclusively at the brain level and is likely to continue to fail as patients experience mood disorders and complications from medications. Accordingly, there is a need for a system and method for treating morbid obesity by restoring or normalizing the appropriate "fullness signals" from the stomach itself as this is the organ that regulates fullness. In particular, the system and method of the invention should cause a feeling of satiety from the stomach itself with less consumption of food by a morbidly obese patient.

SUMMARY

A system and method for treating morbid obesity using a variably cycled percutaneous balloon implanted in the gastric cavity to elicit signals directly from the entire stomach in order to cause a feeling of satiety with less food. This novel approach has the potential to offer a less invasive, more complete elicitation of the feeling of fullness in patients who chronically, and perhaps genetically overeat. The system of the invention includes a balloon device that is contoured to occupy the vast majority of the volume of the stomach. The system also has the capacity to automatically inflate and deflate the balloon, thereby avoiding the problem of pressure induced injury. With the advent of CT scanning and 3-dimensional imaging, patients may have balloons individually designed to meet the specific morphologic features of their stomachs. By fixation of the balloon device, the problems of migration and obstruction are avoided. Furthermore, the system and process of the invention apply appropriate inflation/deflation cycling with a computerized device so as to avoid complications of past devices.

These and other features and advantages of the invention will become more apparent with a discussion of preferred embodiments in reference to the associated drawings.

DRAWINGS

Figure 2:
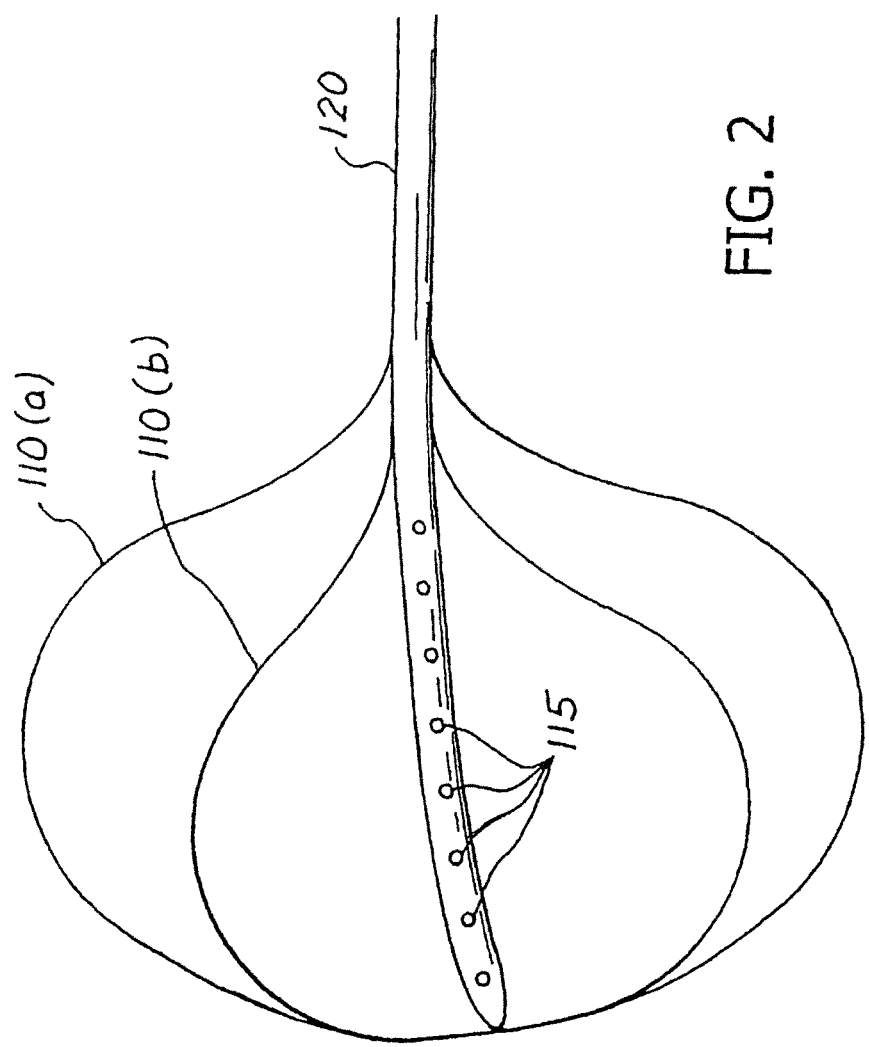

FIG. 1 illustrates a schematic view of a variably cycled percutaneous balloon placed within the gastric cavity of an individual in accordance with an embodiment of the invention; and FIG. 2 illustrates a cross-sectional view of an inflatable balloon and a fillant delivery tube according to the present invention.

DETAILED DESCRIPTION

With reference to FIGS. 1 and 2, a variably cycled percutaneous balloon system 100 for treating morbid obesity is illustrated and comprises an inflatable balloon 110 individually contoured to each patient's stomach, a percutaneous inflation or fillant delivery tube 120 having a proximal end and a distal end connected to the balloon 110, and a control module 130 connected to the proximal end of the tube 120. The tube 120 includes at least one opening 115 for filling the balloon 110 with a biocompatible fillant. The control module 130 variably controls the inflation and deflation of the balloon 110 with the biocompatible fillant such as a liquid, gas, gel or a mixture thereof. In accordance with the teachings of the present invention, the tube 120 is passed through and affixed to abdominal wall 160 and stomach wall 150. The balloon 110 is then positioned into the stomach or gastric cavity 140. The positioning of the balloon 110 may be done, e.g., by the percutaneous endoscopic gastrostomy (PEG) technique, which is known in the art. The balloon 110 and tube 120 may be separate or integral components that are constructed from any surgical grade material. For example, the balloon 110 may be made from latex rubber which expands upon introduction of a fillant, and the tube 120 may be constructed of a metal or plastic material. The tube 120 is connected to the control module 130, which may be a fixed unit or a portable unit mounted to the patient's side. The control module 130 may be a personal computer such as a desktop computer, a laptop computer or a handheld computer. The control module 130 further includes a device such as a pump for introducing and removing a fillant to and from the balloon 110.

A novel feature of the system 100 is it variably controls the inflation and deflation of the balloon 110. For example, the system 100 may inflate and deflate the balloon 110 throughout a predetermined period of time such as a 24-hour period. The balloon 110 would occupy a large volume of the stomach 140 (as shown by reference number 110(a)) when it would be most beneficial for weight loss, and deflate to give the stomach lining a rest (as shown by reference number 110(b)) during less critical time, e.g., during sleeping time. Furthermore, an algorithm tailored to each patient's needs and programmed into the control module 130 is used to control the balloon size to minimize the desire to eat and to prevent blockage or stomach lining necrosis. Unlike the restrictive procedures of the prior art, the variable inflated balloon 110 would not limit nutrient absorption and not lead to altered food choices. This is achieved as the balloon 110 contacts a major portion of the stomach wall 150 when the balloon 110 is fully inflated. Thus, the system 100 of the invention creates a feeling of fullness and satiation by balancing the physiological, neurohormonal and chemical factors.

It will be understood that many modifications can be made to the disclosed embodiments without departing from the spirit and scope of the invention. As such, the above description should not be construed as limiting the invention, but should be interpreted as merely exemplary of preferred embodiments.

The invention claimed is:

1. A method of treating obesity, the method comprising:
    transferring a biocompatible fillant to a gastric device in a gastric cavity to inflate the gastric device, wherein the gastric device comprises—
    an inflatable balloon; and
    a fillant delivery tube extending through the inflatable balloon, wherein a proximal end portion of the fillant delivery tube is connected to a first portion of the balloon and a distal end portion of the fillant delivery tube is connected to a second portion of the balloon spaced apart from the first portion, and wherein the fillant delivery tube is configured to impart a reference shape to the balloon in a deflated state and axially constrain the balloon in an inflated state;
    wherein the biocompatible fillant is transferred to the balloon via the proximal end portion of the fillant delivery tube;
    wherein transferring the biocompatible fillant to the balloon further comprises automatically fully inflating the balloon to a predetermined size with a predetermined volume of the biocompatible fillant; and
    wherein the inflatable balloon comes in contact with a major portion of the gastric cavity when the balloon is in the inflated state such that an outer surface of the inflatable balloon contacts an inner surface of the gastric cavity.

2. The method of claim 1, further comprising delivering the gastric device to the gastric cavity.

3. The method of claim 1, further comprising percutaneously implanting the gastric device in the gastric cavity.

4. A method of claim 1 wherein transferring a biocompatible fillant to the balloon further comprises:
    connecting the proximal end of the fillant delivery tube to an external control module; and
    regulating the inflation of the balloon using the control module.

5. The method of claim 1 wherein transferring the biocompatible fillant to the gastric device further comprises inflating the balloon with the biocompatible fillant such that the gastric device creates a feeling of fullness within a patient.

6. A method of treating obesity, the method comprising:
    transferring a biocompatible fillant to a gastric device in a gastric cavity to inflate the gastric device, wherein the gastric device comprises—
    an inflatable balloon; and
    a fillant delivery tube extending through the inflatable balloon, wherein a proximal end portion of the fillant delivery tube is connected to a first portion of the balloon and a distal end portion of the fillant delivery tube is connected to a second portion of the balloon spaced apart from the first portion, and wherein the fillant delivery tube is configured to impart a reference shape to the balloon in a deflated state and axially constrain the balloon in an inflated state, wherein the biocompatible fillant is transferred to the balloon via the proximal end portion of the fillant delivery tube; and
    contacting a major portion of the gastric cavity with the inflatable balloon when the balloon is in the inflated state such that an outer surface of the inflatable balloon is placed in contact with an inner surface of the gastric cavity.

* * * * *